United States Patent [19]
Allegrini et al.

[11] Patent Number: 5,688,846
[45] Date of Patent: Nov. 18, 1997

[54] SPIRO-PYRANIC COMPOUNDS ENDOWED WITH PHOTOCHROMIC CHARACTERISTICS

[75] Inventors: Pietro Allegrini; Nereo Nodari; Vincenzo Malatesta; Luciana Crisci, all of Milan, Italy

[73] Assignee: Ministero Dell 'Universita' E Della Ricerca Scientifica E Tecnologica, Rome, Italy

[21] Appl. No.: 644,970

[22] Filed: May 15, 1996

Related U.S. Application Data

[62] Division of Ser. No. 241,759, May 12, 1994, Pat. No. 5,532,361.

[30] Foreign Application Priority Data

May 18, 1993 [IT] Italy .................. MI93 A 1012

[51] Int. Cl.$^6$ ............. C07D 413/08; C07D 311/96; C08K 5/15; C08K 5/3417
[52] U.S. Cl. .............. 524/99; 524/109; 524/110; 544/70; 544/230; 549/331
[58] Field of Search ............... 524/109, 110, 524/99; 544/70, 230; 549/331

[56] References Cited

U.S. PATENT DOCUMENTS

| | | |
|---|---|---|
| 3,413,234 | 11/1968 | Taylor et al. |
| 3,578,602 | 5/1971 | Ono et al. .................. 252/300 |
| 4,931,221 | 6/1990 | Heller .................. 549/389 |
| 5,066,818 | 11/1991 | Gemert et al. .................. 549/389 |

FOREIGN PATENT DOCUMENTS

| | | |
|---|---|---|
| 0246114 | 11/1987 | European Pat. Off. |
| 9100861 | 1/1991 | European Pat. Off. |

OTHER PUBLICATIONS

Grant, R. et al. *Grant & Hackh's Chemical Dictionary* (McGraw–Hill, New York), p. 115 (1987).

Rigaudy, J. et al., *IUPAC Nomenclature of Organic Chemistry (Pergamon, Oxford)*, p. 265 (1979).

Primary Examiner—Irina S. Zemel
Attorney, Agent, or Firm—George P. Hoare, Jr.; Rogers & Wells

[57] ABSTRACT

Polymeric compositions comprising a polymer and photochromic compounds belonging to the class of spiro-pyrans, having the general formula (I):

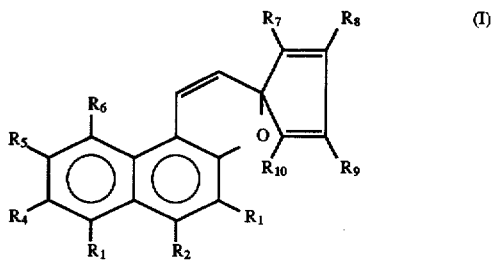

8 Claims, No Drawings

SPIRO-PYRANIC COMPOUNDS ENDOWED WITH PHOTOCHROMIC CHARACTERISTICS

This is a divisional of application Ser. No. 08/241,759, filed May 12, 1994 now U.S. Pat. No. 5,532,361.

FIELD OF THE INVENTION

The present invention relates to novel photochromic compounds.

More particularly, the present invention relates to photochromic compounds belonging to the class of spiro-pyrans, to the process for preparing them and to their use in polymeric materials.

BACKGROUND OF THE INVENTION

The photochromic compounds are substances which display the characteristic of reversibly changing in colour and/or light transmission degree, when they are exposed to some types of electromagnetic radiation and to sun light, returning back to their initial colour and transmission state when the initial light source is removed.

The known substances displaying photochromic characteristics are many and belong to different classes of either organic or inorganic compounds such as, e.g., those described in "Photochromism", by G. H. Brown (Ed.), Volume III of Weissberger "Techniques of Organic Chemistry" Series, Wiley Interscience, New York (1971) and in "Photochromism: Molecules and Systems", by H. Dürr and H. Bouas-Laurent (Ed.), Volume 40 of "Studies in Organic Chemistry" Series, Elsevier (1990).

Among the organic photochromic compounds, those belonging to the classes of spiro-indolino-oxazines, of spiro-pyrans and of chromenes are particularly known.

Said compounds are capable of giving photochromic characteristics to polymerized organic materials, used as photochromic articles as, for example, disclosed in the following commonly assigned Patent Applications: IT 22529 A/87, IT 22660 A/89, IT 19389 A/90, MI 91 A 002038, and in the following commonly assigned U.S. Pat. Nos.: 5,055,576, 5,110,922; and in U.S. Pat. No. 3,567,605; U.S. Pat. No. 5,066,818; and EP 245,020.

The photochromic compounds belonging to the three above cited classes can be suitably mixed, so as to obtain, after exposure to sun light or U.V. light, the development of a colour resulting from the composition of colours of used products. Such a colour composition is particularly useful in the preparation of organic photochromic glasses for which neutral colour shades such as green, brown and grey, are required by the market.

In general, the photochromic compounds used in the field of organic glasses in order to obtain blue or red colour, are those belonging to the class of spiro-indolino-oxazines, thanks to their good characteristics of colour development and fatigue resistance.

On the contrary, yellow and orange colours are obtained by using photochromic compounds belonging to the class of chromenes or spiro-pyrans such as disclosed, e.g., in commonly assigned Italian Patent Applications MI 92 A 002379 and MI 92 A 002492; and in U.S. Pat. No. 5,066,818; U.S. Pat. No. 4,931,221 and EP 250,193.

In fact, although photochromic compounds belonging to the class of spiro-indolino-oxazines capable of developing yellow or orange colours are known as, e.g., disclosed in U.S. Pat. No. 4,816,584, it is known as well that such compounds are difficult to prepare because they form in low yield as reported, e.g., in "Photochromism", by G. H. Brown (Ed.), Volume III of Weissberger "Techniques of Organic Chemistry" Series, Wiley Interscience, New York (1971), p. 244.

However, the photochromic compounds belonging to the class of chromenes or of spiro-pyrans also display some drawbacks. In fact, some photochromic compounds belonging to such classes display a photochromic activity only when the solution or the manufactured article which contains them are cooled down to unacceptably low temperatures.

Furthermore, some photochromic compounds belonging to the class of chromenes or of spiro-pyrans display a too limited ageing resistance as compared to the other photochromic components of the above mentioned mixtures.

A further drawback is given by the poor photochromic activity of those compounds belonging to the class of chromenes or of spiro-pyrans which are capable of developing, by absorbing light of suitable wavelength, shades of yellow color. Such a drawback strongly limits the photochromic activity of compound mixtures suitable for developing such neutral colour shades as green, brown and grey.

In fact, it is well known that the photochromic activity of compounds belonging to classes of spiro-indolino-oxazines, of chromenes and of spiro-pyrans, cannot be arbitrarily increased by increasing the concentration of photochromic compound. Such a correlation is only possible when very low concentrations of active substance are used, whilst, beyond a certain concentration, a threshold value is reached which cannot be exceeded.

On the basis of the above, it is evident that the neutral colour shades should be obtained by limiting the concentration of the photocroms which develop the blue and red colour shades, in order to limit their photochromic effect and thus make it comparable in intensity to the one displayed by the yellow component.

DETAIL DESCRIPTION OF THE INVENTION

The present applicant has now found photochromic compounds belonging to the class of spiro-pyrans, which are capable of developing yellow and/or orange colour shades, which display a better photochromic activity than those known from the prior art, and are capable of overcoming the above described drawbacks.

Therefore, the the present invention provides photochromic compounds belonging to the class of spiro-pyrans, having the general formula (I):

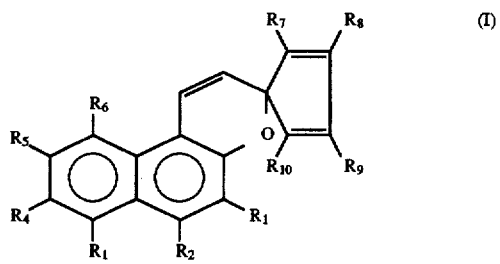

wherein:

(a) the substituents from $R_1$ to $R_{10}$ represent, each independently, a hydrogen atom; a linear or branched $C_1$–$C_5$ alkyl group, possibly substituted with 1–5 halogen atoms selected from fluorine, chlorine, bromine and iodine; hydroxy groups, $C_{1-C_5}$ alkoxy groups, $C_1-C_5$ acyloxy groups; $C_1-C_5$ alkyl-carboxy group, cyano groups; a $C_2-C_5$ alkenyl group; a benzyl group; a halogen atom selected from fluorine, chlorine, bromine and iodine; a hydroxy group; a $C_1-C_5$ alkoxy group; an amino group; a mono-$(C_1-C_5)$-alkyl amino group; a di-$(C_1-C_5)$-alkyl amino group; a $(C_3-C_{10})$-cycloalkyl amino group; a piperidino, piperazino or morpholino group; a carboxy group; a $C_1-C_5$ alkyl carboxy group; a $C_2-C_5$ alkenyl carboxy group; a carboxy-amido group; an N-$(C_1-C_5)$-alkyl-substituted carboxy-amido group; an N,N-di-$(C_1-C_5)$-alkyl-substituted carboxy-amido group; a cyano group; a nitro group; a sulfonic group; a $(C_1-C_5)$-alkyl-sulfonate group; an aryl-sulfonate group; an aryl group selected from phenyl, biphenyl, naphthyl groups; an acyl group of alkyl-ketonic, aryl-ketonic or benzyl-ketonic type;

(b) or, the substituents from $R_7$ to $R_{10}$ alternatively represent, each of them jointly with the adjacent group, an aromatic or heterocyclic ring which can be represented by means of the following formulas (II), (III) and (IV):

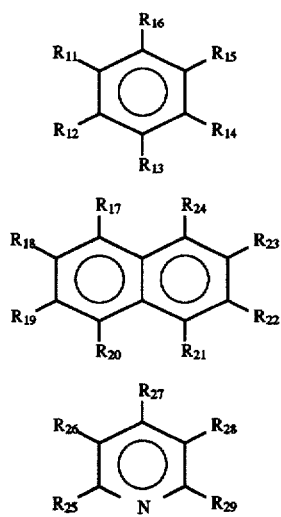

wherein the substituents from $R_{11}$ to $R_{29}$ have the same meanings as disclosed, in point (a) above. Preferred compounds of general formula (I) according to the present invention are those in which:

the substituents from $R_1$ to $R_{29}$, which may be the same or different from each other, represent, each independently, a hydrogen atom, a fluorine, chlorine, bromine atom, a methyl, isopropyl, trifluoromethyl, hydroxymethyl, benzyl, hydroxy, methoxy, amino, piperidino, morpholino, carboxy, carboxymethyl, N,N-dimethylcarboxyamido, cyano, nitro, or phenyl group.

Specific examples of preferred compounds according to the present invention are:

spiro-[3H-naphtho-[2,1b]-pyrano-3,9'-fluorene] (Ia):

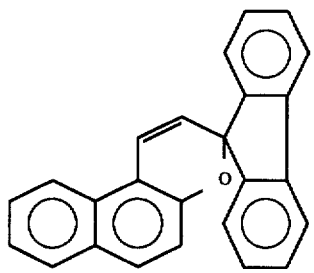

spiro-[3H-naphtho-[2,1b]-pyrano-3,1'-(2',3'-diphenyl)-indene] (Ib):

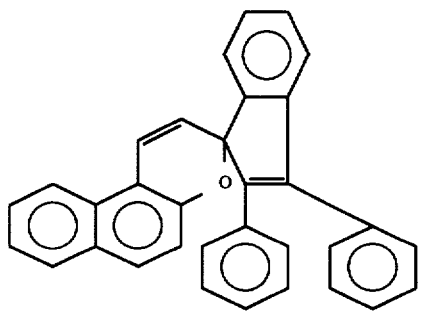

8-methoxy-spiro-[3H-naphtho-[2,1b]-pyrano-3,9'-fluorene] (Ic):

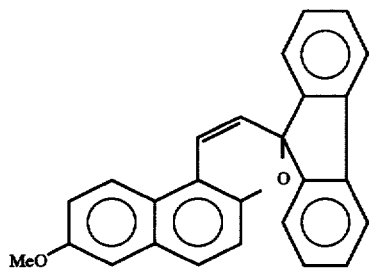

9-methoxy-spiro-[3H-naphtho-[2,1b]-pyrano-3,9'-fluorene] (Id):

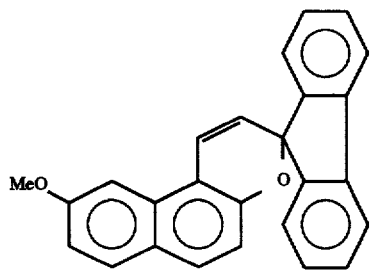

-continued
8-propionyl-spiro-[3H-naphtho-[2,1b]-pyrano-3,9'-fluorene] (Ie):

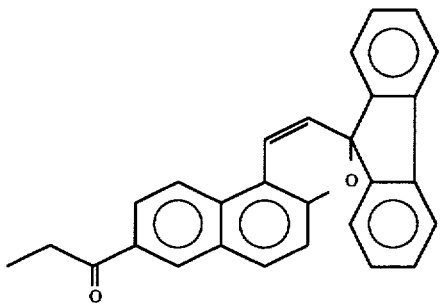

The present invention also relates to a process for preparing the compounds of general formula (I).

The compounds of general formula (I) can be prepared by means of the reduction of the carbonyl group, followed by a dehydration, of compounds of general formula (V):

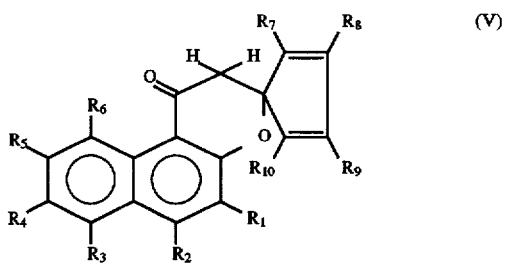

wherein the substituents from $R_1$ to $R_{10}$ have the same meaning as disclosed hereinabove.

The reduction reaction of the carbonyl containing compound of general formula (V) can be carried out according to well known techniques such as catalytic hydrogenation, or using metal hydrides or compounds from the class of boranes, such as, e.g., disclosed in "Chimica Organica Applicata", by U. Valcavi, Ed. CLUED, Milan (1983).

In general, the reduction reaction is carried out in the presence of metal hydrides, such as, e.g., aluminum hydrides and borohydrides, such as: $LiAlH_4$ (lithium aluminum hydride), $AlH_3$ (aluminum hydride), $NaAlH_4$ (sodium aluminum hydride), $i-Bu_2AlH$ (di-isobutyl aluminum hydride), $LiAlH(t-BuO)_3$ (tri-tert.-butoxy lithium aluminum hydride), $NaBH_4$ (sodium borohydride), $(n-C_4H_9)_4NBH_4$ (tetrabutyl ammonium borohydride), $Ca(BH_4)_2$ (calcium borohydride), $LiBH_4$ (lithium borohydride), $NaBH_3(CN)$ (sodium cyano borohydride), and the like.

The above metal hydrides are used in the presence of suitable inert solvents selected, according to the hydride used, from aliphatic or aromatic hydrocarbons (such as pentane, hexane, heptane, benzene, toluene and xylene); chlorinated aliphatic or aromatic hydrocarbons (such as dichloro methane, 1,2-dichloro ethane and chlorobenzene); aliphatic or aromatic ethers (such as diethylene glycol dimethyl ether, diethyl ether, tetrahydrofuran and diphenyl ether); alcohols (such as methanol, ethanol, isopropanol and n-butanol); amides (as dimethyl formamide); esters (such as methyl acetate, ethyl acetate, butyl acetate); carbonates (such as dimethyl carbonate); water; and mixtures of two or more from the above solvents.

The reduction reaction in the presence of metal hydrides can be carried out at a temperature comprised within the range of from 0° C. to 200° C., preferably of from 0° C. to 150° C., and during reaction times comprised within the range of from 1 minute to 200 hours, preferably of from 30 minutes to 50 hours.

The metal hydrides can be used in the reduction reaction in an amount comprised within the range of from 1 to 50 equivalents per each mol of compound to be reduced, preferably of from 1 to 20. Any excess of reducing agent can be removed by adding water or water made acidic by the presence of acids, such as, e.g., sulfuric acid, hydrochloric acid, or still others.

The resulting alcohol can then be purified by chromatography and/or crystallization from suitable solvents such as, e.g., pentane, hexane, heptane, toluene, xylene, ethyl ether, methanol, ethanol, isopropanol, n-butanol, tert.-butanol, tetrahydrofuran, acetone, methylethylketone, ethyl acetate, dimethyl carbonate, acetonitrile, water, and mixtures of two or more from the above solvents.

By operating according to a further method, the alcohol obtained can be submitted to the dehydration reaction directly in the raw reaction mixture.

The dehydration can be carried out by causing the obtained alcohol, as a pure product, or directly in the raw reaction mixture, to react with such acids as, e.g., hydrogen chloride gas or aqueous hydrochloric acid, hydrobromic acid, sulfuric acid, nitric acid, phosphoric acid, acetic acid, trifluoro acetic acid, methane sulfonic acid, p-toluene sulfonic acid, and still others.

According to a preferred procedure, the dehydration reaction is carried out by heating the acidic mixture resulting from the removal of the excess of reducing agent at a temperature comprised within the range of from 0° C. to 200° C., preferably of from 20° C. to 150° C., and during reaction times comprised within the range of from 1 minute to 24 hours, preferably of from 5 minutes to 2 hours.

Water released during the above said dehydration reaction can be possibly removed by azeotropic distillation, by means of a Dean-Stark trap.

The compounds of general formula (I), according to the present invention, can be recovered from the organic solution which contains them by using such known techniques as, e.g., vacuum evaporation of the solvent, and subsequent purification of the resulting raw reaction product by chromatography and/or crystallization.

The crystallization is carried out in the presence of suitable inert solvents selected from aliphatic or aromatic hydrocarbons(such as pentane, hexane, heptane, benzene, xylene); aliphatic or aromatic ethers (such as ethyl ether, tetrahydrofuran); alcohols (such as methanol, ethanol, isopropanol, n-butanol, t-butanol); ketones (such as acetone, methyl ethyl ketone); esters (such as ethyl acetate); carbonates (such as dimethyl carbonate); nitriles (such as acetonitrile); organic acids (such as acetic acid); and mixtures of one or more from the above solvents, with water.

The compounds of general formula (V) are prepared, in their turn, by condensing 2-hydroxy-1-acetonaphthones of general formula (VI):

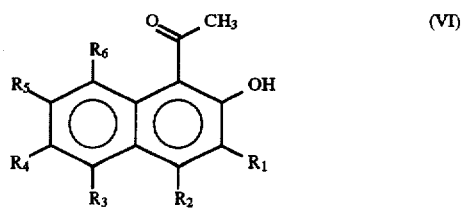

wherein the substituents from $R_1$ to $R_6$ have the above disclosed meaning, with ketonic compounds of general formula (VII):

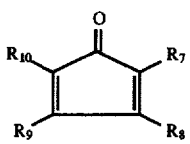

(VII)

wherein the substituents from $R_7$ to $R_{10}$ have the same meaning as disclosed above.

The condensation reaction is carried out by operating according to such conditions as described in technical literature as, e.g., in "Advanced Organic Chemistry", by J. March, 3$^{rd}$ edition, Wiley Interscience (1985) Ed., pages 829–834, and in the references cited in it, or, more specifically, in "Journal of the Chemical Society", by J. Cottam et al., page 5261 (1965).

The condensation reaction is carried out in the presence of compounds of acidic type or, preferably, of basic type. Compounds of basic type useful for the intended purpose, are, e.g., alkali metal alkoxides (such as sodium, potassium methoxide, ethoxide, isopropoxide, tert.-butoxide, and the like); amides (such as sodium amide, lithium amide, lithium diisopropyl amide, N-lithium-(2,2,6,6-tetramethyl) piperidine and the like), alkyl-lithium compounds (such as tert.-butyl lithium); alkali or alkali-earth metal hydrides (such as lithium hydride, sodium hydride, potassium hydride, calcium hydride and the like).

The compounds of basic type can also be used in catalytic or stoichiometric amounts, or even in a large excess over the 2-hydroxy-1-acetonaphthone of general formula (VI).

When the compound of basic type is used in catalytic or stoichiometric amounts, the phenolic function present in the 2-hydroxy-1-acetonaphthone of general formula (VI) must be preliminarily salified with a suitable base.

The salification reaction can be carried out in the presence of the same compounds of basic type as used in the condensation reaction.

On the basis of the above, the compound of basic type can be used in an amount comprised within the range of from 0.05 mol to 12 mol per mol of 2-hydroxy-1-acetonaphthone of general formula (VI), preferably of from 1.1 mol to 5 mol per mol of 2-hydroxy-1-acetonaphthone of general formula (VI).

The molar ratio of 2-hydroxy-1-acetonaphthone of general formula (VI) to the compound of general formula (VII) in the condensation reaction is within the range 0.1 to 6, preferably of from 0.5 to 2.

The condensation reaction can be carried out in the presence of suitable solvents selected, according to the compound of basic type used, from aliphatic or aromatic hydrocarbons (such as pentane, hexane, heptane, benzene, toluene, xylene); chlorinated aliphatic or aromatic hydrocarbons (such as dichloromethane, 1,2-dichloroethane, chlorobenzene); aliphatic or aromatic ethers (such as diethylene glycol dimethyl ether, diethyl ether, tetrahydrofuran, diphenyl-ether); alcohols (such as methanol, ethanol, isopropanol, n-butanol, tert.-butanol); amides (such as dimethyl formamide); dimethyl sulfoxide; mixtures of two or more from the above solvents.

The condensation reaction can be carried out at a temperature within the range of from −78° C. to 200° C., preferably of from 0° C. to 160° C. and during reaction times within the range of from 1 minute to 60 hours, preferably of from 30 minutes to 30 hours.

When the condensation reaction is ended, the compounds of general formula (V) can be obtained by treating the reaction mass with acids such as, e.g., hydrochloric acid, hydrobromic acid, sulfuric acid, phosphoric acid, acetic acid, or mixtures thereof.

The compounds of general formula (V) can be recovered from the organic solution which contains them by using well known techniques such as, e.g., solvent removal by evaporation under vacuum and subsequent purification of the resulting raw product by chromatography and/or crystallization.

The crystallization is carried out in the presence of suitable inert solvents selected from aliphatic or aromatic hydrocarbons (such as pentane, hexane, heptane, benzene, xylene); aliphatic or aromatic ethers (such as ethyl ether, tetrahydrofuran, diphenyl ether); alcohols (such as methanol, ethanol, isopropanol, n-butanol, tert.-butanol); ketones (such as acetone, methylethylketone); esters (such as ethyl acetate); carbonates (such as dimethyl carbonate); nitriles (such as acetonitrile); organic acids (such as acetic acid); and mixtures of one or more of the above solvents, with water.

According to a preferred procedure, the compounds of general formula (V) can be submitted to the reduction reaction disclosed hereinabove, directly in the reaction medium.

According to an alternative route, the compounds of general formula (I) according to the present invention can be prepared by means of a process based on a Claisen rearrangement such as, e.g. disclosed in European Patent EP-246,114.

The compounds of general formula (I) according to the present invention are colourless or pale yellow, yellow-orange or red-coloured crystalline products.

Their solutions in common organic solvents (benzene, toluene, methanol), when not exposed to light sources, are colourless or slightly yellow-coloured.

These solutions, when exposed to an either visible or U.V. light source, turn into intensely yellow-, yellow-orange or reddish coloured.

This deep colour decays rapidly when the light source is removed.

The compounds of general formula (I) can be applied onto the surface, or added to the bulk of the desired articles, by means of techniques known from the prior art, and described in the following.

Some polymeric photochromic articles can be obtained by moulding techniques (e.g., by injection or compression moulding), by starting from the polymers into which the compound of general formula (I) is homogeneously dispersed in bulk.

According to an alternative route, the compound of general formula (I) can be dissolved in a solvent together with the polymeric material, such as, e.g., polymethyl methacrylate, polyvinyl alcohol, polyvinyl butyral, cellulose acetate butyrate, or epoxy, polysiloxanic, urethanic resin. The resulting mixture is deposited onto a transparent support in order to form, after solvent evaporation, a photochromic coating.

The compounds of general formula (I) can also be added to a polymerizable monomer such as, e.g., a meth(acrylic) or allyl carbonate monomer, such that, after polymerization carried out in the presence of a suitable initiator, such as azo-bis-(isobutyronitrile) in the case of the meth(acrylic) monomer or of a peroxyketal in the case of the allyl carbonate monomer, they are uniformly incorporated throughout the formed resin.

Finally, the compound of general formula (I) can be applied onto a transparent substrate such as, e.g., polycarbonate, polymethyl methacrylate or polydiethylene glycol bis(allyl carbonate), by surface impregnation attained by bringing the carrier substrate into contact, at a suitable temperature, with a solution or dispersion containing the compound of general formula (I) according to such methodology as disclosed, e.g. in U.S. Pat. No. 5,130,353.

The compounds of general formula (I) according to the present invention display the feature of being suitable for incorporation, in bulk or by any of the above techniques, in such polymers as high-density polyethylene, low-density polyethylene, ethylene-vinyl acetate copolymer, polyetheramides, polypropylene, polymethyl methacrylate, poly (vinyl alcohol), poly(vinyl butyral), cellulose acetate-butyrate, epoxy, polysiloxanic, or urethanic resins, polycarbonate, polydiethylene glycol bis(allyl carbonate), polyamides, and polyesters.

The compounds of general formula (I) according to the present invention display photochromic activity even at room temperature and, surprisingly, their photochromic activity is higher than those of other products capable of developing similar colours.

The compounds of general formula (I) according to the present invention can be used as mixtures or in combination with suitable organic photochromic compounds in order to obtain, upon activation, neutral colours such as green, brown and grey.

Particularly useful for that purpose are the photochromic compounds belonging to the classes of spiro-indolino-oxazines and of spiro-indolino-pyrans known from the prior art, e.g., from U.S. Pat. No. 5,066,818.

The following experimental examples are reported for the purpose of illustrating the present invention, without being limitative thereof.

EXAMPLE 1

Preparation of Spiro-[3H-naphtho-[2,1b]-pyrano-3', 9'-fluorene] (Ia)

A solution of 9-fluorenone (8.2 g; 45.6 mmol) and 2-hydroxy-1-aceto-naphthone (7 g; 37.6 mmol) in toluene (80 ml) is added in 15 min. to a suspension of sodium amide (3.16 g; 81.2 mmol) in toluene (100 ml) kept at 60° C.

The feed line is washed with 80 ml of toluene. The resulting mixture is heated up to 80° C. and is kept 3 hours at that temperature.

The reaction mass is poured into a mixture consisting of 100 g of crushed ice and 16 ml of 37% hydrochloric acid.

The resulting suspension is stirred until it turns orange and is subsequently diluted with 250 ml of toluene and 200 ml of water. The two phases are separated and the organic one is washed with 200 ml of water before being added, dropwise, to a suspension of sodium borohydride (2 g; 52.8 mmol) in ethanol (40 ml).

The resulting mixture is stirred overnight and then 35 ml of 10% hydrochloric acid is added to it.

The reaction mixture is heated for 1 hour at 45° C. and then 200 ml of water is added and the two phases are separated.

The organic phase is washed with 200 ml of water, thoroughly dried over sodium sulfate and concentrated to dryness. The residue is crystallized from acetone 45 g.

After filtration, the residue is washed with fresh acetone and 6 g of a pale green product is obtained. The product is purified by silica gel column chromatography eluting with toluene.

The product containing fractions are concentrated to 36 g and then are allowed to crystallize at 0° C. After 2 hours at 0° C., the resultant solid is collected by filtration and washed with two 10 ml portions of acetone.

After air drying overnight, 4.5 g (13.6 mmol) of compound (Ia) is obtained as a white solid material having the following characteristics:

melting point (m.p.) (DSC): 222.9° C.; $^1$H-NMR (200 MHz, CDCl$_3$-TMS) δ(ppm): 5.71 (1H, d); 7.04 (1H, d); 7.18–7.26 (2H, m); 7.35–7.73 (10H, m); 7.79 (1H, d); 8.08 (1H, d); Mass Spectrometry (DEP) (m/e): [M$^+$ ion]: 332.

EXAMPLE 2

Preparation of Spiro-[3H-naphtho-[2,1b]-pyrano-3, 1'-(2,3'-diphenyl)indene] (Ib)

A solution of 2-hydroxy-1-acetonaphthone (5 g, 26.9 mmol) and 2,3-diphenyl-1-indenone (8.36 g; 29.6 mmol) in toluene (80 ml) is added dropwise to a suspension of sodium amide (2.26 g; 58 mmol) in toluene (80 ml) kept at 80° C.

The resulting suspension is heated up to 110° C. and is kept 3 hours at this temperature.

The reaction mass is poured into a mixture of 100 g of crushed ice and 20 ml of concentrated hydrochloric acid.

The resulting suspension is stirred for 20 minutes and subsequently diluted with 100 ml of toluene before carrying out the phase separation. The organic phase is washed with 100 ml of water before being added, dropwise, to a suspension of sodium borohydride (3.4 g; 89.76 mmol) in ethanol (50 ml).

The resulting mixture is stirred for one hour at room temperature. Then, 30 ml of 10% hydrochloric acid is added, the resulting mixture is heated at 60° C. for 1 hour and subsequently 100 ml of water is added and the two phases are separated.

The organic phase is washed with 100 ml of water, thoroughly dried over sodium sulfate and concentrated to dryness. The residue is purified by silica gel column chromatography eluting with a mixture of 7:3 (v/v) hexane:toluene.

After product crystallization from toluene, the compound (Ib) is obtained with the following characteristics:

melting point (m.p.) (uncorrected): 198°–200° C.; $^1$H-NMR (200 MHz, CDCl$_3$-TMS) δ(ppm): 5.72 (1H, d); 7.0–7.58 (18H, m); 7.65 (1H, d); 7.78 (1H, d); 8.01 (1H, d); Mass Spectrometry (DEP) (m/e): [M$^+$ ion]: 434.

EXAMPLE 3

Evaluation of the Photochromic Activity of Compounds (Ia) and (Ib)

The photochromic activity in toluene of compounds (Ia) and (Ib), obtained by such modalities as reported in examples 1 and 2, was evaluated and compared to the activity of the compound having formula (R):

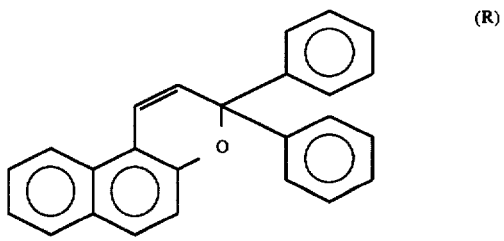

prepared according to such modalities as disclosed in "Journal of the Chemical Society", by J. Cottam et al., page 5261, (1965).

A $10^{-3}$M solution in toluene of the various compounds is prepared and is added to a 1 mm path length quartz cuvette.

The cuvette with the solution is exposed for 30 seconds to the light generated by a Philips UV-A lamp with irradiance of 9 watt/cm² at a fixed distance of 1 cm.

The absorption spectrum of the solution in the region of 400–700 nm. is recorded before and after irradiation with a Hewlett Packard HP8452A photodiode spectrophotometer.

The difference ($\Delta Y$) in light transmittance (Y) of the solution before and after irradiation represents the photochromic activity of the product at the indicated concentrations.

The obtained values are reported in Table 1.

TABLE 1

| Compound | Concentration (× $10^{-3}$ M) | $\Delta Y$ | $\lambda_{max}$* (nm) |
|---|---|---|---|
| (Ia) | 1.05 | 16.18 | 456 |
| (Ib) | 1.06 | 43.6 | 452 |
| (R) | 1.05 | 6.03 | 430 |

*$\lambda_{max}$: wavelength corresponding to the absorption maximum in the visible range, of the activated form.

As one may observe from Table 1, the compounds according to the present invention display a $\Delta Y$ higher than that of the compound known from the prior art, and are hence endowed with a higher photochromic activity.

EXAMPLE 4

Preparation of Photochromic Lenses by Bulk Addition

Three photochromic lenses are prepared according to the process disclosed in commonly assigned Patent Application MI 92 A 002492.

The allyl carbonate used is obtained from the reaction of diallyl carbonate (DAC) with a mixture of neopentyl glycol (NPG) and tris(hydroxyethyl) isocyanurate (THEIC) in the following proportions: NPG 70% by weight; THEIC 30% by weight; DAC/(NPG+THEIC) molar ratio=5:1.

The resulting product is a complex mixture containing:
monomeric neopentyl glycol bis(allyl carbonate) and oligomers thereof;
monomeric tris(hydroxyethyl)-isocyanurate tris(allyl carbonate) and oligomers thereof;
mixed allyl carbonate of neopentyl glycol and tris(hydroxyethyl)-isocyanurate.

The above said product displays the following chemical-physical characteristics:

viscosity, 25° C. (cst): 80;

density, 20° C. (g/ml): 1.1411;

$n_D^{20}$: 1.4595.

The liquid polymerizable compositions are prepared by blending and homogenizing allyl carbonate (98.4%), 1,1-di(tert.-butyl peroxy)-3,3,5-trimethylcyclohexane perketal (1.5%) and the photochromic compound (R) or (Ia) respectively disclosed in examples 3 and 1.

The resulting compositions are used in order to fabricate, by polymerization, lenses of 2 mm of thickness, by means of the conventional casting technique. According to such a technique, the catalyzed liquid composition is cast into the hollow of a mould consisting of two glass elements with a spacer gasket of plasticized polyvinyl chloride or ethylene-vinyl acetate (EVA) copolymer.

The liquid composition is submitted to polymerization inside the mould by heat treatment, in a forced circulation oven, during 5 hours at 85° C., plus 15 hours at 90° C. and 7 further hours at 100° C. At the end of this treatment, the moulds are opened, the polymerized articles are recovered and on the resulting photochromic lenses the following characteristics are determined:

photochromic properties, determined by recording the UV-A-visible spectra at 23° C. of the deactivated and activated forms, by means of a Hewlett Packard HP8452A spectrophotometer (activation by 60-second irradiation with a UV-A lamp having an irradiance of 9 W/m²). The following values of the unactivated and activated forms are recorded:

(a) O.D. ($\lambda_{max}$ UV-A) and O.D. ($\lambda_{max}$ visible): values of optical density at absorption maximum wavelength $\lambda_{max}$ in the UV-A and visible regions, respectively;

(b) Y: value of tristimulus colorimetry, which indicates the value of light transmittance in the visible region, as defined by the CIE standard 1931. Such a value is obtained by mathematical processing of the absorption spectra of said activated and unactivated forms;

(c) photochromic activity: expressed as $\Delta Y$, which represents the difference between the light transmittance values.

In Table 2, the data are reported which relate to the photochromic lenses obtained by using the photochromic compound (Ia), together with those relating to the photochromic lenses obtained by using the photochromic compound (R) known from the prior art.

TABLE 2

| | Unactivated form | | | Activated form | | |
|---|---|---|---|---|---|---|
| Compound | O.D. in UV-A region ($\lambda_{max}$) | O.D. in visible region ($\lambda_{max}$) | Y | O.D. in visible region ($\lambda_{max}$) | Y | $\Delta Y$ |
| (Ia) | 1.233 (366 nm) | 0.1073 (454 nm) | 88.73 | 1.346 (454 nm) | 66.65 | 22.06 |
| (R) | 1.993 (360 nm) | 0.1898 (418 nm) | 95.21 | 0.8916 (418 nm) | 86.00 | 9.21 |

O.D. = Optical density
$\lambda_{max}$ = Wavelength corresponding to the absorption maximum As one may observe from Table 2, the compound according to the present invention displays a higher $\Delta Y$ than the $\Delta Y$ of the compound known from the prior art, and therefore displays a higher photochromic activity.

EXAMPLE 5

Preparation of 9-Ethinyl-9-hydroxy-fluorene (A1)

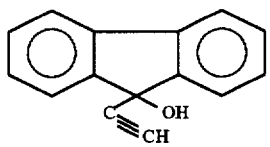

9 g (0.05 mol) of 9-fluorenone and 100 ml of anhydrous THF are charged into a dry flask of 250 ml. To the resulting solution a suspension of sodium acetylide [17.8 g (0.0525 mol) in mineral oil/xylene, 18% by weight based on the suspension; solid purity 95%] is added under nitrogen, by means of a syringe. The resulting suspension is kept overnight under nitrogen and with stirring before being poured into 75 ml of 10% HCl. The phases are separated and the aqueous phase is extracted twice with 100 ml of ethyl ether. The organic extracts are combined and thoroughly dried over sodium sulfate. By eliminating the solvent, 10.1 g of product is obtained, which is used without any further purification.

EXAMPLE 6

Preparation of 8-Methoxy-spiro[3H-naphtho-[2,1b]-pyrano-3,9'-fluorene] (Ic)

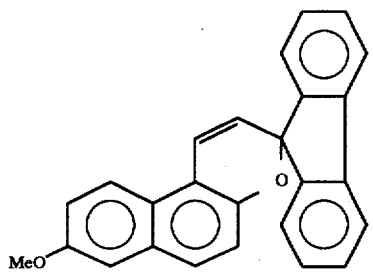

142 mg of para-toluene sulfonic acid is added to a suspension of 6-methoxy-2-naphthol (1.5 g; 8.6 mmol) and 9-ethinyl-3-hydroxy-fluorene (A1) (1.6 g; 7.77 mmol) in toluene (70 ml). The resulting mixture is stirred overnight at room temperature. The resulting suspension is filtered off to give a clear solution. The toluene solution is washed with 70 ml of 5% NaOH and then with 50 ml of water. The organic phase is thoroughly dried over sodium sulfate and concentrated to dryness. The residue is chromatographed on silica gel (25 g) using a mixture 2:1 (v/v) hexane:toluene as eluent. The product containing fractions are concentrated to dryness and the residue is recrystallized with a mixture of 2:1 (v/v) toluene:heptane. After filtration, hexane washing and vacuum drying, 620 mg of (Ic) is obtained.

Mass Spectrometry (DIS) (m/e): [M$^+$ ion]: 362. H$^1$-NMR (200 MHz, CDCl$_3$-TMS) δ(ppm); 3.93 (3H, s, OCH$_3$); 5.71 (H,d, CH of the pyran ring); 7.07 (H, d); 7.12 (H, d); 7.17–7.3 (3H, m); 7.33–7.46 m); 7.55 (3H, d); 7.66 (2H, d); 7.99 (H, d).

EXAMPLE 7

Preparation of 9-Methoxy-spiro[3H-naphtho-[2,1b]pyrano-3,9'-fluorene](Id)

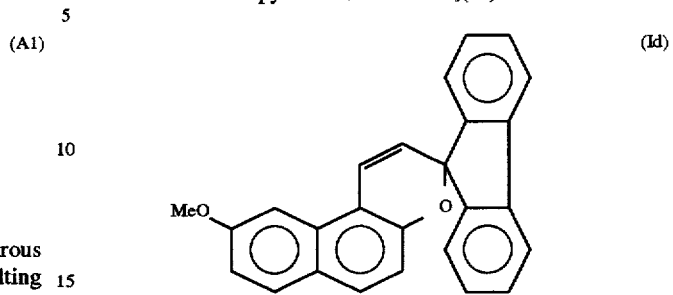

130 mg of para-toluene-sulfonic acid is added to a suspension of 7-methoxy-2-naphthol (1.5 g; 8.6 mmol) and 9-ethinyl-9-hydroxy-fluorene (A1) (1.6 g; 7.76 mmol) in toluene (50 ml). The resulting mixture is stirred for 2 hours at room temperature and washed twice with 100 ml of water.

The resulting organic phase is thoroughly dried over sodium sulfate and the solvent is removed on a rotavapor. The residue is chromatographed on silica gel (30 g), using toluene as the eluent. The pure product containing fractions are combined and concentrated to dryness. The residue is chromatographed once more on silica gel (100 g), using a mixture of 12:1 (v/v) hexane:acetate as eluent. The product containing fractions are concentrated to dryness, and the residue is crystallized from ethyl acetate. The product (Id) (60 mg) is thus obtained with the following characteristics:

Mass Spectrometry (DIS (m/e): [M$^+$] 362. $^1$H NMR (200 MHz, CDCl$_3$-TMS) δ(ppm); 3.98 (3H, s, OCH$_3$); 5.71 (H, d); 6.9 (H, d); 7.06(H,dd); 7.19–7.28 (2H,m); 7.33–7.45 (4H, m); 7.53–7.61 (3H, m); 7.63–7.72 (3H, m).

EXAMPLE 8

Preparation of 6-Propionyl-2-naphthol (A2)

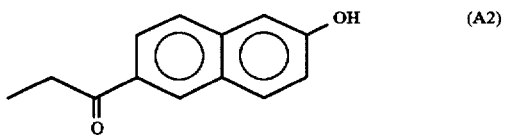

To a solution of 10 g of 2-methoxy-6-propionylnaphthalene, prepared according to J. Chem. Soc. (1934), p. 864, in acetic acid (45 ml) and kept under reflux, 47 ml of aqueous HBr (48% by weight) is added during a three-hour time period. The resulting suspension is poured onto 500 g of crushed ice; the formed tars are left in the reaction flask. A suspension is obtained which is filtered on a Buchner filter. The solid material is washed with 100 ml of water, 50 ml of saturated aqueous solution of NaHCO$_3$, and then with 50 ml of water. After drying in air and in oven at 60° C. for 10 hours, 5.3 g of pink-white product is obtained with the following characteristics:

m.p. 158°–9° C. (uncorrected); $^1$H-NMR (200 MHz, CDCl$_3$-TMS) δ(ppm); 1.18 (3H, t, CH$_3$); 3.1 (2H, q, CH$_2$); 7.1–7.3 (2H, m, aromatic H); 7.75 (1H, d, aromatic H); 7.85–8.05 (2H, m, aromatic H); 8.53 (1H, s, aromatic H); 8.95–9.3 (1H, bs, hydroxy H).

EXAMPLE 9

Preparation of 8-Propionyl-spiro[3H-naphtho-[2,1b] pyrano-3,9'-fluorene] (Ie)

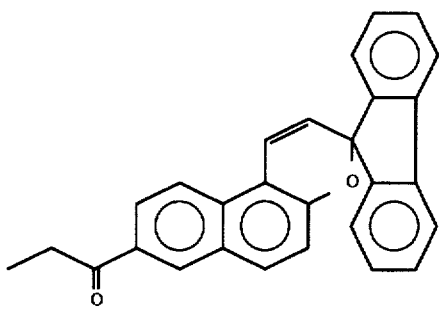

(Ie)

100 mg of methane sulfonic acid is added to a suspension of 6-propionyl-2-naphthol (A2) (2.13 g; 10.6 mmol) and 9-ethinyl-9-hydroxy-fluorene (A1) (1.6 g; 7.76 mmol) in toluene (57 ml). The resulting mixture is stirred for 24 hours at room temperature and the resultant solid is collected by filtration.

From the resulting clear solution the solvent is removed under reduced pressure and the residue is chromatographed twice on a silica gel column, eluting, in the first run, with a 1:1 (v/v) mixture of toluene:hexane, and in the second run, with a 95:5 (v/v) mixture of hexane:ethyl acetate. The product containing fractions are concentrated to dryness and the residue is crystallized from hexane. In this way, the product (Ie) is obtained as a slightly yellowish white solid having the following characteristics:

Mass Spectrometry (GCMS) (m/e): [M$^+$ ion]: 388; $^1$H-NMR (200 MHz, CDCl$_3$-TMS) δ(ppm): 1.3 (3H, t, C$\underline{H_3}$CH$_2$CO—); 3.15 (2H, q, CH$_3$C$\underline{H_2}$CO); 5.74 (H, d); 7.1 (H, d); 7.18–7.29 (2H, m); 7.35–7.48 (3H, m); 7.54 (2H, d); 7.68 (2H, d); 7.78 (H, d); 8.11 (2H, s); 8.42 (H, s).

EXAMPLE 10

Evaluation of the Photochromic Activity of Compounds (Ia), (Ic), (Id) and (Ie) in Hexane The photochromic activity in hexane of compounds (Ia), (Ic), (Id) and (Ie), obtained according to such modalities as reported in examples 1 and 5–9, was evaluated as compared to the activity of the compound having formula (R) described in example 3.

A 10$^{-4}$M solution of the several compounds in hexane is prepared and is added to a 1-cm path length quartz cuvette.

The cuvette with the solution is irradiated fop 90 seconds with a Philips UV-A lamp with an irradiance of 9 watt/cm$^2$, placed at a fixed distance of 1.5 cm.

The photochromic characteristics of the several products are evaluated as disclosed in example 3.

The obtained values are reported in following Table 3.

TABLE 3

| Compound | Concentration (× 10$^{-4}$ M) | ΔY | λ$_{max}$* (nm) |
|---|---|---|---|
| (Ia) | 1.02 | 22.01 | 446 |
| (Ic) | 0.99 | 42.19 | 474 |
| (Id) | 1.05 | 24.95 | 436 |

TABLE 3-continued

| Compound | Concentration (× 10$^{-4}$ M) | ΔY | λ$_{max}$* (nm) |
|---|---|---|---|
| (Ie) | 1.01 | 19.88 | 454 |
| (R) | 1.08 | 8.15 | 420 |

*λ$_{max}$: wavelength corresponding to the maximum of absorption in the visible range of the activated form.

As one may observe from Table 3, the compounds according to the present invention display a higher ΔY than the ΔY of the compound known from the prior art, and are hence endowed with a higher photochromic activity.

EXAMPLE 11

Evaluation of the Photochromic Activity of Compounds (Ie), (Ic) and (Id) in Methanol.

The evaluations disclosed in the preceding example are repeated in methanol. The results are gathered in Table 4.

TABLE 4

| Compound | Concentration (× 10$^{-4}$ M) | ΔY | λ$_{max}$ (nm) |
|---|---|---|---|
| (Ie) | 1.08 | 21.58 | 454 |
| (Ic) | 1.05 | 39.05 | 486 |
| (Id) | 1.05 | 23.93 | 452 |
| (R) | 1.02 | 16.31 | 432 |

As one may observe from Table 4, the compounds according to the present invention display a higher ΔY than the ΔY of the compound known from the prior art, and are hence endowed with a higher photochromic activity.

EXAMPLE 12

Preparation of Organic Photochromic Lenses

Photochromic lenses of poly[diethylene glycol bis(allyl carbonate)] containing the compounds (Ia), (Ic) and (R) are prepared by means of a technique of surface impregnation.

Such a technique consists of preparing a suspension of the photochromic product in question at 10–15% by weight in silicone oil (WACKER AK 100; d$_{25°}$ c=0.97; viscosity at 25° C.=100 cst).

The photochromic product is finely dispersed throughout the silicone oil by using a ball mill and the resulting suspension is further diluted with the same oil, until a concentration of 4% of photochromic compound is obtained.

One g of the resulting dispersion is charged on the upper part of a horizontally placed glass mould.

On said mould a lens of poly[diethylene glycol bis(allyl carbonate)] is placed, so as to form a thin layer of photochromic dispersion between the mould and the lens.

The so prepared assembly is charged, in horizontal position, to a forced-circulation oven and is submitted to a 2-hour heat treatment.

The transfer temperature of the photochromic product from the dispersion to the lens depends on the characteristics of the used product, and is reported in Table 5.

After this treatment, the lens is recovered, is cleaned with hexane or petroleum ether and finally with acetone. On the so obtained photochromic lenses, the same characteristics as disclosed in example 4, are determined.

In table 5, the data relevant to the photochromic lenses obtained from compounds (Ia) and (Ic) are reported, as compared to those displayed by the compound (R) known from the prior art.

TABLE 5

| Compound | Lens impregnation temperature (°C.) | Unactivated form | | | Activated form | | |
|---|---|---|---|---|---|---|---|
| | | O.D. in UV-A region ($\lambda_{max}$) | O.D. in visible region ($\lambda_{max}$) | Y | O.D. in visible region ($\lambda_{max}$) | Y | ΔY |
| (Ia) | 170 | 1.961 (366 nm) | 0.055 (458 nm) | 90.80 | 1.063 (458 nm) | 60.60 | 30.19 |
| (Ic) | 160 | 1.577 (382 nm) | 0.072 (496 nm) | 88.40 | 1.249 (4.96 nm) | 35.81 | 52,59 |
| (R) | 140 | 1.962 (360 nm) | 0.040 (432 nm) | 91.86 | 0.866 (432 nm) | 73.42 | 18.44 |

O.D. = Optical density
$\lambda_{max}$ = Wavelength corresponding to the absorption maximum As one may observe from Table 5, the compounds according to the present invention display a higher ΔY than the ΔY of the compound known from the prior art, and are hence endowed with a higher photochromic activity.

We claim:

1. A polymeric composition comprising a polymer and a photochromic compound having the formula (I):

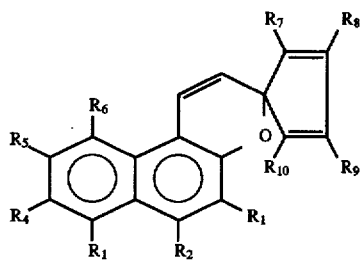

wherein:

(a) $R_1$ to $R_{10}$ are independently selected from the group consisting of hydrogen; linear and branched $C_1$–$C_5$ alkyl groups, optionally having 1–5 halogens; hydroxy groups; $C_1$–$C_5$ alkoxy groups; $C_1$–$C_5$ acyloxy groups; carboxy-$C_1$–$C_5$ alkyl groups; cyano groups; $C_2$–$C_5$ alkenyl groups; benzyl groups; halogens; amine groups; mono-($C_1$–$C_5$)-alkyl amino groups; di-($C_1$–$C_5$)-alkyl amino groups; ($C_3$–$C_{10}$)-cycloalkyl amino groups; piperidino, piperazino, and morpholino groups; carboxy groups; $C_2$–$C_5$ alkenyl carboxy groups; aminocarbonyl groups; N-($C_1$–$C_5$)-alkyl-substituted aminocarbonyl groups; N,N-di-($C_1$–$C_5$)-alkyl-substituted aminocarbonyl groups; nitro groups; sulfonic groups; ($C_1$–$C_5$)-alkyl-sulfonate groups; aryl-sulfonate groups; aryl groups selected from the group consisting of phenyl, biphenyl, and naphthyl groups; and carbonyl groups selected from the group consisting of alkyl carbonyls, phenyl carbonyls, naphthyl carbonyls and benzyl carbonyls; wherein the halogen is fluorine, chlorine, bromine, or iodine; or (b) each of the substituents from $R_7$ to $R_{10}$ alternatively represents, jointly with the group adjacent thereto, a ring structure having a formula selected from the following formulas (II), (III) and (IV):

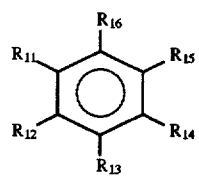

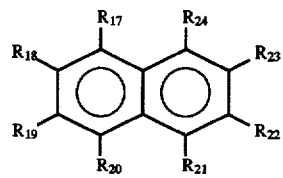

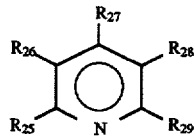

and substituents $R_1$ to $R_6$ and $R_{11}$ to $R_{29}$ represent the same groups contained by $R_1$ to $R_{10}$ in part (a).

2. A polymeric composition comprising:

(A) at least one polymer selected from the group consisting of polyethylene, ethylene-vinyl acetate copolymer, polyether-amine, polypropylene, polymethyl methacrylate, poly(vinyl alcohol), poly(vinyl butyral), cellulose acetatebutyrate, epoxy, polysiloxanic, urethanic resins, polycarbonate, polydiethylene glycol bis (allyl carbonate), polyamides, polyesters and mixtures thereof;

(B) a photochromatic compound having the formula (I):

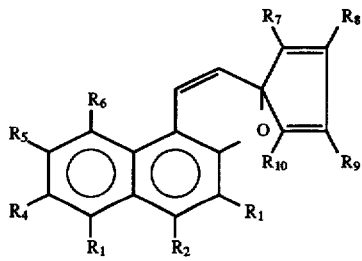

wherein:

(a) $R_1$ to $R_{10}$ are independently selected from the group consisting of hydrogen; linear and branched $C_1$–$C_5$ alkyl groups, optionally having 1–5 halogens; hydroxy groups; $C_1$–$C_5$ alkoxy groups; $C_1$–$C_5$ acyloxy groups; carboxy-$C_1$–$C_5$ alkyl groups; cyano groups; $C_2$–$C_5$ alkenyl groups; benzyl groups; halogens; amine groups; mono-($C_1$–$C_5$)-alkyl amino groups; di-($C_1$–$C_5$)-alkyl amino groups; ($C_3$–$C_{10}$)-cycloalkyl amino groups; piperidino, piperazino, and morpholino groups; carboxy groups; $C_2$–$C_5$ alkenyl carboxy groups; aminocarbonyl groups; N-($C_1$–$C_5$)-alkyl-substituted aminocarbonyl groups; N,N-di-($C_1$–$C_5$)-alkyl-substituted aminocarbonyl groups; nitro groups; sulfonic groups; ($C_1$–$C_5$)-alkyl-sulfonate groups; aryl-sulfonate groups; aryl groups selected from the group consisting of phenyl, biphenyl, and naphthyl groups; and carbonyl groups selected from the group consisting of alkyl carbonyls, phenyl carbonyls, naphthyl carbonyls and benzyl carbonyls; wherein the halogen is fluorine, chlorine, bromine, or iodine; or (b) each of the substituents from $R_7$ to $R_{10}$ alternatively represents, jointly with the group adjacent thereto, a ring structure having a formula selected from the following formulas (II), (III) and (IV):

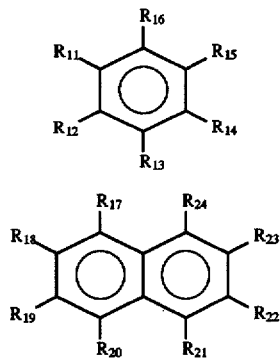

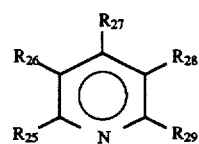

and substituents $R_1$ to $R_6$ and $R_{11}$ to $R_{29}$ represent the same groups contained by $R_1$ to $R_{10}$ in part (a).

3. The polymeric composition of claims 1 or 2, wherein $R_1$ to $R_{29}$ are independently selected from the group consisting of hydrogen, fluorine, chlorine, bromine, methyl, isopropyl, trifluoromethyl, hydroxymethyl, benzyl, hydroxy, methoxy, amino, piperidino, morpholino, carboxy, carboxymethyl, N,N-dimethylcarboxy amido, cyano, nitro, and phenyl.

4. The polymeric composition according to claims 1 or 2, wherein aid photochromic compound is spiro-[3H-naphtho[2,1b]-pyrano-3,9'-fluorene].

5. The polymeric composition according to claims 1 or 2, wherein aid photochromic compound is spiro-[3H-naphtho-[2,1b]-pyrano-3,1')-2',3'-diphenyl)-indene].

6. The polymeric composition according to claims 1 or 2, wherein said photochromic compound is 8-methoxy-spiro-[3H-naphtho-[2,1b]-pyrano-3,9'-fluorene].

7. The polymeric composition according to claims 1 or 2, wherein said photochromic compound is 9-methoxy-spiro-[3H-naphtho-[2,1b]-pyrano-3,9'-fluorene].

8. The polymeric composition according to claims 1 or 2, wherein said photochromic compound is 8-propionyl-spiro-[3H-naphtho-[2,1b]-pyrano-3,9'-fluorene].

* * * * *